United States Patent
Xia (10) Patent No.: US 11,148,116 B2
(45) Date of Patent: Oct. 19, 2021

(54) METHODS AND APPARATUS FOR SYNTHESIZING COMPOUNDS BY A LOW TEMPERATURE PLASMA DUAL-ELECTRIC FIELD AIDED GAS PHASE REACTION

(71) Applicant: HyChar Energy, LLC, Newton, MA (US)

(72) Inventor: Yashen Xia, Newton, MA (US)

(73) Assignee: HyChar Energy, LLC, Newton, MA (US)

( * ) Notice: Subject to any disclaimer, the term of this patent is extended or adjusted under 35 U.S.C. 154(b) by 282 days.

(21) Appl. No.: 16/107,423

(22) Filed: Aug. 21, 2018

(65) Prior Publication Data
US 2019/0055655 A1    Feb. 21, 2019

Related U.S. Application Data

(60) Provisional application No. 62/605,621, filed on Aug. 21, 2017.

(30) Foreign Application Priority Data

Sep. 7, 2017    (CN) ................... 201710801710.8
Sep. 7, 2017    (CN) ................... 201710801807.9
(Continued)

(51) Int. Cl.
*B01J 19/08*      (2006.01)
*C25B 1/02*      (2006.01)
(Continued)

(52) U.S. Cl.
CPC .......... *B01J 19/088* (2013.01); *B01D 5/0057* (2013.01); *B01J 19/1843* (2013.01);
(Continued)

(58) Field of Classification Search
CPC ..... C25B 1/02; C07C 29/1512; B01D 5/0057; B01D 2257/108; B01J 19/1843;
(Continued)

(56) References Cited

U.S. PATENT DOCUMENTS 2,583,898 A * 1/1952 Smith ..................... H01J 37/32
                                                204/168
2,907,707 A * 10/1959 Wintermute ........... B01J 19/088
                                            422/186.04
(Continued)

FOREIGN PATENT DOCUMENTS

WO    WO-0043102 A2 * 7/2000 ............ B01J 19/088

*Primary Examiner* — Nicholas A Smith
(74) *Attorney, Agent, or Firm* — Novick, Kim & Lee, PLLC; Allen Xue (57) ABSTRACT

Method and apparatus for synthesizing compounds by a low temperature plasma dual-electric field aided gas phase reaction are provided. The method utilizes two different electrode corona discharge fields in a plasma aided reactor to form a plasma dual-electric field, using electric energy to convert gas into gas molecules, atoms, ions and/or free radicals, and then reforming and reducing to obtain organic compounds such as aliphatic hydrocarbons, higher carbon ethers, higher carbon alcohols, higher carbon esters, lower carbon alcohols, and the like; also inorganic compounds such as $N_2$, $O_2$, $H_2SO_4$, $NH_3$, and the like. The apparatus includes a reactor having a plasma region of two different corona discharge fields, wherein an alternating current corona discharge field or a positive corona discharge field is set in the first electric field, and a negative corona discharge field is set in the second electric field.

14 Claims, 1 Drawing Sheet

(30) Foreign Application Priority Data

| Sep. 7, 2017 | (CN) | 201710801808.3 |
|---|---|---|
| Sep. 7, 2017 | (CN) | 201710802457.8 |
| Sep. 7, 2017 | (CN) | 201710802459.7 |
| Oct. 18, 2017 | (CN) | 201710978477.0 |

(51) Int. Cl.

| B01J 19/18 | (2006.01) |
|---|---|
| B01D 5/00 | (2006.01) |
| C07C 29/151 | (2006.01) |
| C01B 3/24 | (2006.01) |

(52) U.S. Cl.
CPC .......... *C07C 29/1512* (2013.01); *C25B 1/02* (2013.01); *B01D 2257/108* (2013.01); *B01J 2219/00198* (2013.01); *B01J 2219/0801* (2013.01); *B01J 2219/0809* (2013.01); *B01J 2219/0828* (2013.01); *B01J 2219/0841* (2013.01); *B01J 2219/0849* (2013.01); *B01J 2219/0875* (2013.01); *B01J 2219/0892* (2013.01); *B01J 2219/0896* (2013.01); *C01B 3/24* (2013.01); *C01B 2203/0216* (2013.01); *C01B 2203/0272* (2013.01); *C01B 2203/04* (2013.01); *C01B 2203/0475* (2013.01); *C01B 2203/061* (2013.01); *C01B 2203/062* (2013.01); *C01B 2203/0861* (2013.01); *C01B 2203/1229* (2013.01)

(58) Field of Classification Search
CPC .............. B01J 19/088; B01J 2219/0892; B01J 2219/0841; B01J 2219/0849; B01J 2219/0828; B01J 2219/0809; B01J 2219/00198; B01J 2219/0875; B01J 2219/0896; B01J 2219/0801; C01B 2203/061; C01B 2203/0475; C01B 2203/04; C01B 2203/0272; C01B 2203/062; C01B 2203/0861; C01B 2203/1129; C01B 2203/0216; C01B 3/24
USPC .................................................. 422/186–187
See application file for complete search history.

(56) References Cited

U.S. PATENT DOCUMENTS

| 3,205,162 | A | * | 9/1965 | MacLean | B01J 19/088 422/186.04 |
|---|---|---|---|---|---|
| 3,451,910 | A | * | 6/1969 | Hellund | B01J 19/088 204/168 |
| 5,004,587 | A | * | 4/1991 | Tacchi | C01B 13/11 422/186.07 |
| 5,458,856 | A | * | 10/1995 | Marie | B29C 59/12 422/186.07 |
| 5,503,809 | A | * | 4/1996 | Coate | B01J 19/088 422/186.07 |
| 5,516,493 | A | * | 5/1996 | Bell | C01B 13/11 422/186.07 |
| 5,630,915 | A | * | 5/1997 | Greene | B01J 19/088 422/186.21 |
| 5,836,154 | A | * | 11/1998 | Williamson | B01D 53/32 422/186.04 |
| 6,159,432 | A | * | 12/2000 | Mallinson | B01J 19/088 422/186.04 |
| 2014/0046494 | A1 | * | 2/2014 | McAlister | G06F 1/26 700/287 |
| 2018/0236426 | A1 | * | 8/2018 | Finlay | B01J 19/088 |
| 2019/0252700 | A1 | * | 8/2019 | Miura | B01J 19/08 |

* cited by examiner

METHODS AND APPARATUS FOR SYNTHESIZING COMPOUNDS BY A LOW TEMPERATURE PLASMA DUAL-ELECTRIC FIELD AIDED GAS PHASE REACTION

This application claims the benefit of U.S. Provisional Application No. 62/605,621 filed in Aug. 21, 2017, Chinese Application No. 201710978477.0 filed in Oct. 18, 2017, Chinese Application No. 201710802457.8 filed in Sep. 7, 2017, Chinese Application No. 201710802459.7 filed in Sep. 7, 2017, Chinese Application No. 201710801808.3 filed in Sep. 7, 2017, Chinese Application No. 201710801807.9 filed in Sep. 7, 2017, Chinese Application No. 201710801710.8 filed in Sep. 7, 2017, the contents of which are hereby incorporated by reference in their entirety.

FIELD OF THE INVENTION

The disclosure belongs to the non-thermodynamic equilibrium plasma technology, and particularly plasma-aided chemical reaction.

BACKGROUND OF THE INVENTION

A plasma is a collection of electrons, ions, atoms, free radicals, and molecules formed from gas molecules which are excited by energy such as heat or electric fields, wherein, the positive and negative charges are basically the same, so as to be called as plasma. According to the plasma energy state, temperature and ion density, it can be divided into high temperature, heat and cold plasma. In cold plasma, electrons can have kinetic energy of more than 5 eV, and molecules, free radicals and atoms can be in the range from room temperature to several hundred degrees. The electrons with sufficient energy can react with the gas molecules in an inelastic collision to convert them into active particles such as excited particles, free radicals (or atoms) and ions, so that the reactants are activated, and the catalytic reactions that are difficult to perform in kinetics can be carried out at lower temperature.

Common cold plasma generation techniques include silent discharge, corona discharge, glow discharge, microwave discharge and radio frequency discharge. Wherein silent discharge and corona discharge can produce cold plasma at atmospheric pressure. The corona discharge can produce high-energy electrons at low temperatures by using asymmetric electrode discharge, while the silent discharge is gas discharge with insulation medium existing between the electrodes, and the insulating medium can avoid spark or arc discharge between the electrodes.

SUMMARY OF THE INVENTION

Methods and apparatus for synthesizing compounds by a low temperature plasma dual-electric field aided gas phase reaction are described. The method of the present disclosure utilizes two different electrode corona discharge fields in a plasma aided reactor to form a plasma dual-electric field, using electric energy to convert gas into gas molecules, atoms, ions and/or free radicals, and then reforming and reducing to obtain organic compounds such as aliphatic hydrocarbons, higher carbon ethers, higher carbon alcohols, higher carbon esters, lower carbon alcohols, and the like; also inorganic compounds such as $N_2$, $O_2$, $H_2SO_4$, $NH_3$, and the like. The apparatus of the present disclosure includes a reactor having a plasma region of two different corona discharge fields, for example, a first electric field and a second electric field sequentially connected, wherein an alternating current corona discharge field or a positive corona discharge field is set in the first electric field, and a negative corona discharge field is set in the second electric field, that is, strong oxidation firstly occurs under the action of electrons, and then strong reduction and reforming are performed to produce a target product. Various gas molecules such as $CH_4$, $CO_2$, CO, $O_2$, $H_2$, $H_2S$, $H_2O$, $SO_2$, and $NO_x$ (including, for example, NO and $NO_2$) may be used in the alternating current corona discharge field or the positive corona discharge field, in which oxidation or decomposition occurs to generate various active components such as $O_3$, $H^-$, H, $CH_3$ and CO, and in the subsequent negative corona discharge field, the molecules, atoms, ions, and/or free radicals of gases produced by oxidation or decomposition tend to entrain electrons in a large population of electrons that are densely erupted, rapidly aggregate and collide, and are forcedly reduced and reformed into more stable products. The products may, include one or more organics selected from the following group consisting of, for example, aliphatic hydrocarbons (e.g., heptane, hexadecane, octadecane, and eicosane), higher carbon ethers (e.g., ethylene glycol monododecyl ether), higher carbon alcohols (e.g., dodecanol, tetradecanol), higher carbon esters (e.g., methyl hexadecanate, methyl octadecanoate, dibutyl phthalate, diisooctyl phthalate, methyl oleate, methyl linoleate, and the like), lower carbon alcohols (e.g., $CH_3(OH)$, $C_2H_5(OH)$, and the like) and $CO(NH_2)_2$; and inorganic compounds, for example, $N_2$, $O_2$, $H_2SO_4$, $NH_3$, and the like.

The present disclosure provides a method for the plasma dual-electric field aided reforming gas phase reactions, comprising the following steps: the reaction gas is introduced into a reactor, containing corona discharge dual-electric field, which includes a first electric field and a second electric field, wherein the first electric field is an alternating current corona discharge field or positive corona discharge field or other electric field sources which can provide sufficient energy to oxidize and decompose the various gas molecules in the reaction gas into atoms, ions, and free radicals, and the second electric field is a negative corona discharge field.

Preferably, the positive corona discharge field is a high voltage positive direct current corona discharge field, further preferably is a high frequency and high voltage positive direct current corona discharge field.

Preferably, the negative corona discharge field is a high voltage negative direct current corona discharge field, further preferably is a high frequency and high voltage negative direct current corona discharge field.

The present disclosure adopts the non-thermodynamic equilibrium plasma technology, the gas molecules are excited by the electric field energy to form an assembly of electrons, ions, atoms, radicals and molecules. In cold plasma, the electrons may have a kinetic energy of about 4-6 eV, electrons with sufficient energy may incur inelastic collision with the gas molecules to convert them into active particles such as excited particles, free radicals (or atoms) and ions, etc., so as to activate the reactants. Corona discharge can use asymmetric electrodes to generate plasma under atmospheric pressure discharge, dielectric barrier discharge can discharge at the pressure of atmospheric pressure or even above atmospheric pressure in a gap of an insulating medium, to generate repeated electron to collide with the medium, so as to increase the current density, strengthen the electric field strength, thereby causing a violent chemical reaction. The speed of the electrons inside the plasma generated in this way is very fast and the temperature of the electrons inside the plasma generated in this way is very high (for example, 11000K) and the temperature of the gas is close to room temperature, thus forming a thermodynamic imbalance, which causes the reaction system to free from the thermodynamic equilibrium composition limit and maximize the conversion of all reactants into products. On the one hand, the electrons of the electrode have energy high enough to excite, dissociate and ionize the reactant molecules, and promote the reaction molecules and ions to fully react in a short time to be transformed into products, on the other hand, the reaction gas may be able to maintain low temperature, even close to room temperature, so as to allow the low temperature gas molecules to effectively obtain the thermodynamic energy for chemical decomposition or synthesis to quickly react, thus reducing the energy consumption of unnecessary high temperature and high pressure processing.

It should be pointed out that such a dual-electric field excitation reaction system can both abandon or reduce the use of the catalyst, and make it possible to avoid the application of high temperature and high pressure process equipment as much as possible. In the traditional catalytic process, people often have to heat some complex metal catalyst particles by high temperature and high pressure to activate the electrons on the surface of the metal catalyst material, thereby constructing an excited state micro-electric field of large specific surface area to direct and compress gas molecules around the surface of the aggregated particles for rapid decomposition and reforming. However, the plasma dual-electric field aided excitation reaction technique of the present disclosure makes it possible to artificially allow all gas oxidation and reduction reactions to obtain electric energy without a catalyst, and to achieve positive or negative electromagnetization in a polar strong electromagnetic field space and rapidly aggregate, and rapidly perform decomposition and reforming. Meanwhile, this method also provides a thermodynamically optimized selection and process opportunity for efficient oxidation and reduction, or decomposition and reforming of the reaction gases to achieve a stable end point of products without being bound by any thermodynamic equilibrium composition.

The plasma alternating current corona field, the negative corona discharge field and the positive corona field of the present disclosure are not particularly limited, and any plasma source known in the art can be used in the present disclosure.

According to the present disclosure, the main function of the alternating current corona discharge field or the positive corona discharge field is oxidation and reforming to decompose gas molecules into ions and other free radicals, which actually constitutes a strengthened gas oxidation electric field, wherein any gas molecules and charged particles are forcibly oxidized by the influence of a positive ion field or an alternating electric field. Subsequently, the negative ions and molecules are reduced and converted into new molecules in the negative corona discharge field, that is, a strengthened reduction electric field is actually constructed, so that the molecules and charged particles in the dense free electron group can be forcibly reduced and reformed, and different gas molecules and charged particles can be rapidly reduced. In fact, this corona discharge dual-electric field can reform or envelop high-energy electrons into the outer orbit of the decomposed molecules or ions to produce new particles with different bond energies, making them a storage medium for electrical energy. This corona discharge field plasma aided reaction process technique makes it possible to artificially apply the polarity of the positive or negative electric field to effectively carry out a chemical process of strong oxidation or strong reduction.

It should be noted that when the first electric field is an alternating current corona discharge field, the gas may be decomposed or oxidized in the positive higher half band of the alternating current corona discharge field, and subjected to reduction and reforming in the negative lower half band. However, the polarity of such an electric field alternates rapidly at high frequencies. Since the alternating frequency is too high (such as 20 kHz), and some product molecules require more time to reform than that required for the reaction molecules to decompose, the oxidatively decomposed particles do not necessarily have time to be reduced in response to changes in the negative electric field. Even if some of the particles are reduced and reformed to a compound in the lower half band of the negative polarity, they will immediately decompose in the next positive polarity band, and thus a stable product cannot be obtained. Therefore, it is not possible to achieve a stable product preparation by separately setting an alternating current corona discharge field. Moreover, a large amount of experimental evidence does show that the total effect of the alternating current corona discharge field is often close to that of the positive corona discharge field.

According to the present disclosure, a reactive gas is introduced into the reactor, first through an alternating current corona discharge field or a positive corona discharge field, and then through a negative corona discharge field to eject electrons to supply energy to the gas molecules. Electrons are provided to bombard gas molecules in the alternating current corona discharge field or the positive corona discharge field, thereby decomposing gas molecules or causing molecules to lose electrons, and under the action of the positive corona discharge field (electrons will flow back to the positive electrode), the compound loses oxygen atoms, forming decomposed small molecules, positive ions or free radicals thus being oxidized. Taking $CO_2$ as an example, in this region, $CO_2$ is subjected to an electron-addition reaction to form CO and $O_2$. In the region of the negative corona discharge field, the corona discharge is performed on the electrode of the negative corona discharge field, releasing a large amount of negative electrons to adhere to the surface of the molecule, and CO and $H_2$ gas molecules capture these high-energy electrons to form high-energy electronegative gas ions, for example, negative ions such as $H^-$, $CO^-$ or $H^-$. These negative ions will be forced to be re-reduced or reformed into another stable compound, such as an organic or inorganic compound, while releasing oxygen to achieve minimal system energy.

In the present disclosure, the reaction gas includes, but is not limited to, at least one of $CH_4$, $CO_2$, CO, $O_2$, $H_2$, $H_2S$, $H_2O$, $SO_2$ and $NO_x$ (including, for example, NO and $NO_2$), and the source thereof is not particularly limited, for example, it may be from a gas produced by a combustion device, a carbon source energy gas containing methane, or a gas generated by a gas generating device, such as natural gas, coalbed methane, biogas, shale gas, water gas, coke oven gas, flue gas, automobile exhaust gas, and the like.

Preferably, the reaction gas is specifically: coalbed methane and water vapor, or shale gas and oxygen or carbon dioxide, or biogas, or coke oven gas, or flue gas and water vapor, or water gas or syngas optionally mixed with hydrogen.

As an example, in the above-mentioned gas as a mixed gas, in the region of the alternating corona discharge electric field or the positive corona discharge electric field, the following reactions may mainly occur:

$$CO_2 + e^- ===> CO + \tfrac{1}{2}O_2^-$$

$$CO + H_2O + e^- ===> CO_2 + H_2^-$$

$$CH_3 + H_2O + 3e^- ===> CO + 3H_2^-$$

$$CH_4 + CH_2 + 2e^- ===> 2CO + 2CH_2^-$$

$$CH_4 + \tfrac{1}{2}O_2 2e^- ===> CO + 2H_2^-$$

$$H_2O + e^- <===> OH^- + H^-$$

$$2SO_2 + 2H_2O + 3O_2 + 2e^- ===> 2H_2SO_4 + 2O_2^-$$

$$NO_x + x/2e^- ===> \tfrac{1}{2}N_2 + x/2O_2^-$$

$$NO_x + e^- ===> N + xO + e^-$$

$$2H_2S + 3O_2 + e^- ===> 2SO_2 + 2H_2O + e^-$$

In the area of the negative corona discharge electric field, the following reactions mainly occur:

$$H_2 + 2e^- ===> 2H^- ===> H_2^-$$

$$2N + 2O + e^- ===> N_2 + O_2^-$$

$$N_2 3H_2^- ===> 2NH_3^-$$

$$4NO + 6H_2O + 5e^- ===> 4NH_3 + 5O_2^-$$

$$CO_2 + 2NH_3 + e^- ===> CO(NH_2)_2 + H_2O^-$$

$$2CO + 3H_2^- ===> C_2H_5(OH) + O_2^- + 5e^-$$

$$CO + 2H_2^- ===> CH_3(OH) + 2e^-$$

$$(n+1)H_2^- + nCO ===> C_nH_{(2n+2)} + n/2O_2 + 2(n+1)e^-$$

In the present disclosure, the reaction gas is reformed to obtain a mixed gas, and the content of each component in the product obtained is slightly different according to the difference of the raw material gas, but under normal operating conditions, the reformed mixed gas is condensed by a condenser and separated into two phases of gas and liquid.

Taking the reaction mixed gas mainly containing CO as an example, after the mixed gas obtained by reforming is separated by condensation, the gas phase is still mainly CO which has not yet reacted, and the main product in the liquid phase is mainly determined by the strength of the plasma electric field in the apparatus in which the reaction is carried out. For example, when the reaction electric field is a strong electric field, it produces organic compounds such as aliphatic hydrocarbons, higher carbon ethers, higher carbon alcohols, and higher carbon esters, when the reaction electric field is a weak electric field, it mainly produces lower carbon alcohols such as ethanol and methanol.

In order to increase conversion, a plurality of dual-electric field reactors may be connected in series, and the unconverted gas components may be further reformed to synthesize the target product. For example, in order to synthesize more organic compounds and inorganic compounds, hydrogen or water vapor may be directly added to the reactor to reform the reaction gas. By operating in this way, almost all of the carbon oxides can be converted stepwise into organic compounds. In a similar way, for the other target products required, the same method is employed, such as direct addition of water vapor, reforming of the reaction gas, and the like.

Although for the chemical processing, AC-negative dual-electric field and positive-negative dual-electric field may be more widely used, according to the needs of production, people can reversely place the corona discharge dual-electric field to form a negative-positive electric field, to meet the requirement of carrying out gas reduction before decomposition and reforming. For example, a negative-positive dual-electric field is constructed, the first electric field is a negative electric field, wherein $CO_2$ and water vapor are reduced to produce ethanol first, and then in the second electric field of positive corona field, the ethanol is decomposed into CO and hydrogen, and thus pure hydrogen is obtained after the separation of CO, so as to achieve the purpose of hydrogen production, which is used to provide hydrogen fuel cell for driving a car or provide large-scale hydrogen fuel.

The apparatus used in the present disclosure is not particularly limited, and as described above, the alternating corona discharge electric field or the positive corona discharge electric field and the negative corona discharge electric field may be any known devices of the prior art.

The present disclosure does not particularly limit the apparatus to be used, particularly, as mentioned above, any known apparatus in the prior art may be used for the alternating current corona discharge field or the positive corona discharge field and the negative corona discharge field. Preferably, the dual-electric field apparatus of the present disclosure is as follows:

The apparatus has corona discharge dual-electric field, wherein a first electric field at least one of: alternating current corona discharge field, a positive corona discharge field, and other electric discharge field sources which can provide sufficient energy to oxidize and decompose various gas molecules into atom, ion, free radicals, etc., and a second electric field which is a negative corona discharge field.

According to the present disclosure, it is preferable that the first electric field is a positive corona discharge field.

According to the present disclosure, it is preferable that the positive corona discharge field is a high voltage positive direct current corona discharge electric field, such as a high frequency and high voltage positive direct current corona discharge electric field.

According to the present disclosure, it is preferable that the negative corona discharge field is a high voltage negative direct current corona discharge electric field, such as a high frequency and high voltage negative direct current corona discharge electric field.

According to the present disclosure, the positional relation between the first electric field and the second electric field is not particularly limited, and for example, the first electric field may be placed at an upper portion of the apparatus or may be placed at a lower portion of the apparatus; correspondingly, the second electric field may be placed at the lower portion of the apparatus or may be placed at an upper portion of the apparatus.

According to the present disclosure, the gas may pass through the first electric field firstly, then the product mixture obtained by the first electric field treatment further enters the second electric field, or the gas may pass through the second electric field firstly, then the product mixture obtained by the second electric field treatment further enters the first electric field, as a result, different electric field setting sequences can achieve different gas processing purposes.

Preferably, the order for the gas passing through the dual-electric field is set as: first into the alternating current corona discharge field or positive corona discharge field and then into the negative corona discharge field, that is, alternating current-negative corona discharge dual-electric field or positive-negative corona discharge dual-electric field, or the order for the gas passing through the dual-electric field is set as: first into the negative corona discharge field and then into the alternating current corona discharge field or positive corona discharge field, that is negative-alternating current corona discharge dual-electric field or negative-positive corona discharge dual-electric field.

Preferably, the apparatus has a housing in which a reaction chamber is disposed, wherein at least one of the reaction chambers has an alternating current corona discharge field or a positive corona discharge field, and at least one of the other reaction chambers has a negative corona discharge field. An electrode or a metal rod is disposed at the center of the corona discharge field, and the alternating current corona discharge field source or the positive corona discharge field source and the negative corona discharge field source supply electric power to the electrode or the metal rod, and the electrodes or metal rods provide high-energy electrons that can be adsorbed to the gas.

Preferably, the housing of the apparatus is ground connection.

Preferably, the apparatus has a gas inlet and a gas outlet, wherein the gas inlet is for charging a gas into the reaction chamber of the corona discharge dual-electric field, and the gas outlet is for removing the gas product.

Preferably, a condensing separator in connection with the gas outlet is provided outside the reactor, and the condensing separator has a liquid outlet and a gas outlet.

As described above, the product of the dual-electric field apparatus of the present disclosure is determined by the electric field strength, and when it is a strong electric field, it produces organic compounds such as aliphatic hydrocarbons, higher carbon ethers, higher carbon alcohols, higher carbon esters, and inorganic compounds, when the electric field is a weak electric field, it mainly produces lower carbon alcohols such as ethanol and methanol. It is well known in the art that the intensity of the plasma electric field is related to factors such as the applied voltage, the distance between the positive and negative electrodes, and whether or not the dielectric medium is added.

Therefore, those skilled in the art can adjust the above characteristics in the dual-electric field apparatus according to actual production requirements to obtain a strong electric field or a weak electric field to produce different organic or inorganic substances. The following are several specific examples of the strong electric field or the weak electric field according to the present disclosure.

As an example, the reaction chamber is a metal cylindrical reaction chamber or a metal tubular reaction chamber; a center electrode or a central metal rod is disposed in the center of the metal cylindrical reaction chamber or the metal tubular reaction chamber, and a counter electrode or a counter metal rod is disposed on the outer wall of the metal cylindrical reaction chamber or the metal tubular reaction chamber, and at this time, a strong electric field is generated in the corona discharge dual-electric field. The positive electric field in the strong electric field can be used to oxidize and decompose gas molecules, and the negative electric field is mainly used for reducing and reforming into organic compounds, such as aliphatic hydrocarbons, higher carbon ethers, higher carbon alcohols, higher carbon esters, and the like, and can also be used to synthesize inorganic compounds.

Preferably, the center electrode or the central metal rod is connected to a negative electrode of a negative corona discharge field source, and the counter electrode or the counter metal rod is connected to a positive electrode of the negative corona discharge field source, to generate a strong negative electric field, and/or the center electrode or the central metal rod is connected to a positive electrode of an alternating current corona discharge field source or a positive corona discharge field source, and the counter electrode or the counter metal rod is connected to a negative electrode of the alternating current corona discharge field source or the positive corona discharge field source, to generate a strong positive electric field.

As an example, the reaction chamber is a metal cylindrical reaction chamber or a metal tubular reaction chamber; a center electrode or a central metal rod is disposed in the center of the metal cylindrical reaction chamber or the metal tubular reaction chamber, and a counter electrode or a counter metal rod is disposed at the distal end (such as the ground), and at this time, a weak electric field is generated in the corona discharge dual-electric field. The weak electric field is used to produce organic compounds, for example, lower carbon alcohols such as methanol or ethanol.

Preferably, the center electrode or the central metal rod is connected to a negative electrode of a negative corona discharge field source, and the counter electrode or the counter metal rod is connected to the ground, to generate a weak negative electric field, and/or the center electrode or the central metal rod is connected to a positive electrode of an alternating current corona discharge field source or a positive corona discharge field source, and the counter electrode or the counter metal rod is connected to the ground, to generate a weak positive electric field.

Preferably, the alternating current corona discharge field or the positive corona discharge field and the negative corona discharge field are arranged above and below. The electric field into which the gas is first introduced is placed in the lower part, that is, the lower part of the apparatus. The electric field into which the gas is introduced later is placed at the upper part, that is, the upper part of the apparatus. The gas inlet is at the bottom of the apparatus, and the gas outlet is at the top of the apparatus.

Preferably, a thin layer tube of insulating medium may be placed between the center electrode or the central metal rod and the outer wall of the metal cylindrical reaction chamber or the metal tubular reaction chamber, and the insulating medium tube may be made of materials with different dielectric constants, for example, glass, ceramic, silica gel, wood, bamboo, and the like. A gas nip channel is formed between the thin layer tube of the insulating medium and the outer wall, that is, a dielectric barrier discharge (DBD) structure is formed, reinforcing the electric field strength of the metal cylindrical reaction chamber and the metal tubular reaction chamber, thereby strengthening the reaction process.

Figure 1:
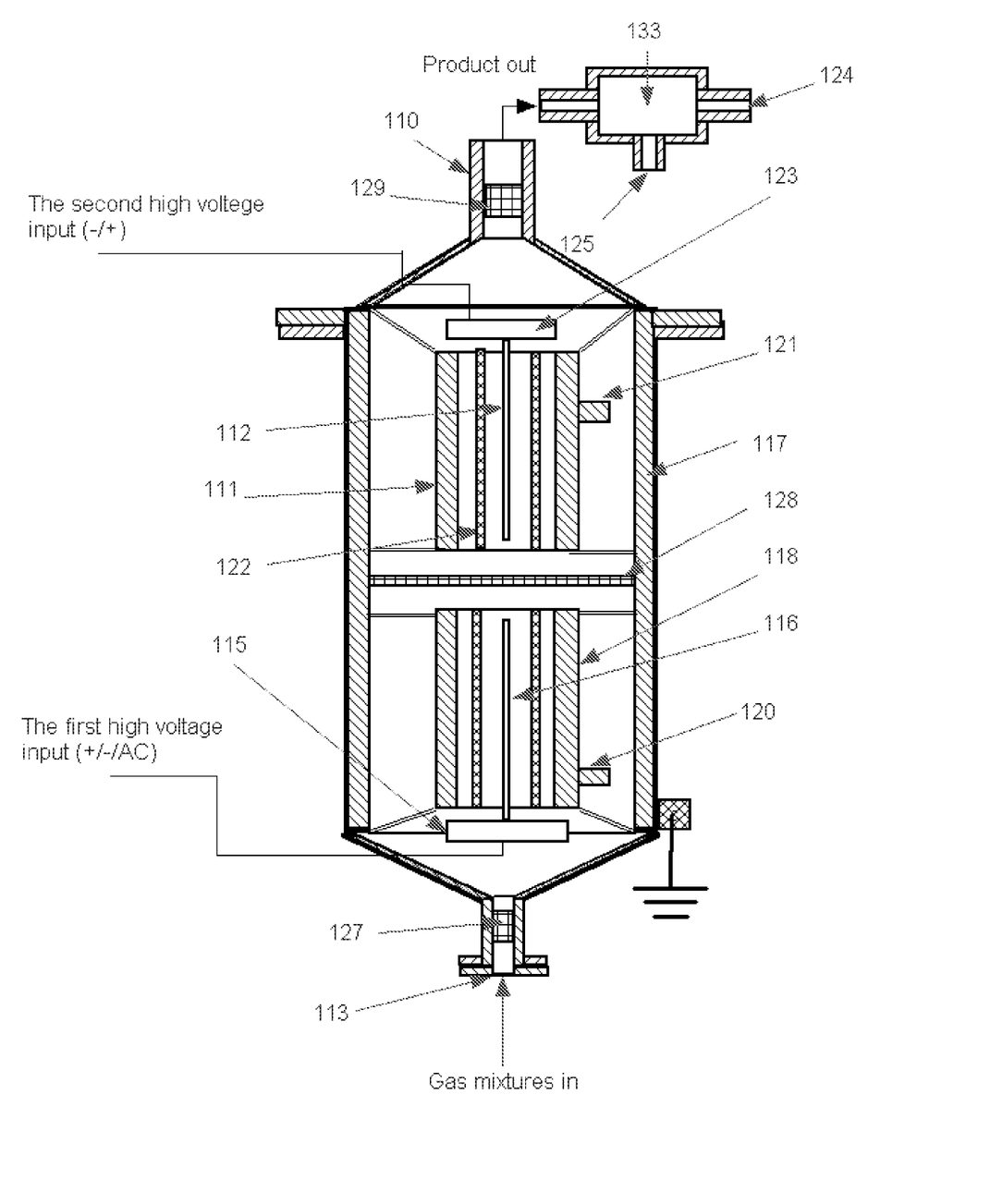
FIG. 1 is a schematic view showing a specific configuration of an apparatus for plasma aided gas phase reaction according to the present disclosure.

Preferably, the diameter and the number of the metal cylindrical reaction chamber and the metal tubular reaction chamber are not particularly limited, and may be a conventional choice of those skilled in the art, for example, as shown in FIG. 1, one metal cylinder reaction chamber may be used, or two or more metal cylinders or metal tubes may be used to form a reaction tube series. When a plurality of metal cylinders or metal tubes are selected, they have no influence on each other, so the arrangement thereof is not particularly limited, and a reasonable selection can be made according to the size of the apparatus.

Preferably, in each electric field segment, the number of metal cylindrical reaction chambers or metal tubular reaction chambers is one or more, and a plurality of metal cylindrical reaction chambers or metal tubular reaction chambers are arranged to form a group of cylindrical or tubular tube series.

Preferably, the diameter of the metal cylinder reaction chamber or the metal tube reaction chamber is not particularly limited, and may be, for example, a metal cylinder or a metal tube having a large diameter (for example, more than 70 mm), or a large number of metal cylinders or metal tubes having a small diameter (for example, 30-70 mm). The specific choice also needs to be reasonably made based on the electric field strength and the amount of gas to be treated.

Furthermore, it is well known to those skilled in the art that the relative size of the metal cylinder or metal tube diameter also affects the electric field strength within the reaction chamber. For example, when a center electrode or a central metal rod is disposed in the center of the metal cylindrical reaction chamber or the metal tubular reaction chamber, and the counter electrode or the counter metal rod is disposed on the outer wall of the metal cylindrical reaction chamber or the metal tubular reaction chamber, if a large diameter metal cylinder or metal tube is used, at this time, the distance between the positive and negative electrodes of the electric field is larger than that of a small diameter metal cylinder or metal tube, so the internal electric field strength is smaller than that formed inside the small diameter metal cylinder or metal tube. Similarly, the electric field strength can also be adjusted by the introduction of the medium, the addition of the insulating medium layer to the electric field having a weak electric field strength greatly enhances the electric field strength of the electric field. Therefore, those skilled in the art can reasonably design the electric field strength in the first electric field and the second electric field according to the factors, such as diameter of the metal cylindrical reaction chamber or the metal tubular reaction chamber, the dielectric constant of the insulating medium substance, the voltage of the external power supply, and the like, and then carry out the preparation of different organic compounds and inorganic compounds.

Preferably, gas filters are placed between the first and the second fields and near the gas inlet and the gas outlet. The gas filters are preferably be a material having a physical and/or chemical adsorption function, for example fiber filters, a particle (such as activated carbon or molecular sieves) packed bed, a tourmaline granule packed bed (generally having the function of decomposing moisture in the air to produce trace amounts of hydrogen to reduce ozone).

Preferably, a partition is provided between each of the upper and lower surfaces of the corona discharge dual-electric field and the housing of the apparatus for blocking and closing, so that the gas passage is unique.

Preferably, the number of the center electrodes is one or more, and the electrodes may be, for example, saw tooth tip electrodes to generate the dual-electric field of an alternating corona discharge electric field or a positive corona discharge electric field around the electrodes and a negative corona discharge electric field around the electrodes.

In some instances, the electrode is a linear or needle-shaped element with a sharp point at the tip of the electrode. The sharp point provides a very high charge area around it. The electrode can be nickel, iron, steel, tungsten, carbon or platinum. The disclosure is not limited to a particular type of electrode material, any material that can form a corona discharge to produce electrons.

The electrode in the reaction chamber generates electrons by forming an alternating current corona discharge field or a negative corona discharge field at the tip of the electrode or negative electrode. The electrons are generated in the corona of the electrode tip. These electrons are adsorbed on the chemical gas molecules around the tip of the electrode. In the dual-electric field apparatus of the present disclosure, as for the metal material suitable for the electrodes in the corona discharge apparatus, the energy required to migrate the electrons from the surface of the corona electrode is about 4-6 eV. The electrodes may be of the following materials: nickel, iron, steel, tungsten, carbon or platinum. The present disclosure does not make any particular limitation to the electrode material, and any material that can form corona to generate electrons can be used. The electrodes may also be coated with a metal catalyst, and the noble metal catalysts available are: gold, nickel, rhodium, cobalt, phosphorus, cesium and platinum. Any noble metal catalyst capable of producing electrons can be used.

Preferably, the shape of the electrode can be linear or needle-shaped. If the electrode has a sharp point, that is, the potential difference of the gas near the sharp point is much higher than at other positions around the electrode. Eventually, the resulting high potential electronegative ions will transfer the charge to the adjacent low potential region, so as to reform a gas molecule.

Preferably, the principle and arrangement of the metal rod are the same as the electrode.

Preferably, the metal rod is selected from thin metal rods.

Other sources that allow electrons to have sufficient energy to transfer to a gas may also be used in the present disclosure. Electronegative gas ions can also be generated by other non-thermal or thermal plasma technologies or negative ion sources, including high frequency processes such as radio frequency plasma, microwave plasma inductively coupled plasma, and the like, such as electron beam (EB). Any method capable of generating electronegative gas ions with sufficient energy to react with the gas can be used in the present disclosure.

The operating conditions of the method and apparatus for plasma aided gas phase reaction of the present disclosure are as follows: it can be operated at atmospheric pressure, and the reaction gas is involved in the reforming reaction in gaseous state. Gas processing amount can be arbitrarily selected, the power input will increase as the number of discharge metal cylinders or metal tubes in the reactor increases and the amount of gas processed increases, and the voltage may be 3000 to 300,000 volts, preferably 10,000 to 200,000 volts, for example 15,000 volts, and the frequency is 15 to 35 kHz, preferably 20 kHz, 25 kHz or about 35 kHz. It should be understood that the above conditions are of the preferred operating conditions of the present disclosure, but the key to achieving the method and object of the present disclosure is the use of a plasma dual-electric discharge field itself. These operating conditions may be determined by routine experimentation and are not limited to the specific description described above.

According to the present disclosure, when the main component of the gas introduced into the dual-electric field device is $CH_4$, it is necessary to detect and control the entering concentration of the mixed gas before the gas enters the dual-electric field apparatus. For example, the methane, oxygen concentration sensor and valve are installed in the intake line before the reaction gas enters the dual-electric field apparatus. Once the sensor detects that the concentration of methane gas and oxygen in the mixture is close to the explosion limit, the valve will be closed to prevent the methane concentration from burning. The explosion point concentration eliminates any possibility of entering the reactor with an oxygen-containing explosive mixture. When the methane and oxygen concentrations are in a safe zone, the gas will pass through the valve into the dual-electric field apparatus.

In some embodiments, when the product mixed gas produced by the dual-electric field apparatus contains a large amount of water vapor in addition to ethanol, the product mixed gas is introduced into the condensing separator for gas-liquid separation, and the residual methane and other non-condensable gases are recycled to participate in the reforming, and the liquid containing ethanol and water is separated from the gas and transported to the next stage, for example, to the atmospheric distillation column for rectification to form ethanol with a high concentration.

In a specific embodiment, the aqueous ethanol solution obtained by the reforming of the apparatus of the present disclosure may be up to 83% or more, preferably up to 95% ethanol concentration after rectification.

The present disclosure also provides a use of a dual-electric field apparatus in the preparation of organic and inorganic compounds.

Preferably, the carbon source-containing gas is an energy gas mainly containing methane or a gas mixture mainly containing CO and $CO_2$, which is reformed into an organic compound. The carbon source-containing gas is, for example, coalbed methane, mash gas, shale gas, biogas, flue gas, coke oven gas, refinery exhaust gas, automobile or internal combustion engine exhaust gas, water gas, syngas, natural gas, and the like.

The present disclosure also provides a use of a dual-electric field apparatus in the preparation of hydrogen.

Preferably, the apparatus reduces $CO_2$ and water vapor to produce ethanol, then decomposes the ethanol into CO and hydrogen, and hydrogen is obtained after the separation of the CO.

The present disclosure also provides a use of a dual-electric field apparatus in the purification and cleaning of the gas.

In particular, the apparatus is used for purifying and cleaning, removing carbon, removing sulfur and/or removing nitride of exhaust gases containing CO, $CO_2$, sulfides and/or nitrides.

In addition, other advantages obtained from the method and apparatus of the present disclosure will be apparent to those skilled in the art based on the disclosure of the present disclosure. Other aspects and advantages of the present disclosure will be described in detail below in the detailed description.

DESCRIPTION OF THE PREFERRED EMBODIMENT

The disclosure will now be further described with reference to specific embodiments. It should be understood that these examples are merely illustrative of the disclosure and are not intended to limit the scope of the disclosure. In addition, it should be understood that various changes and modifications may be made to the present disclosure after reading the teachings of the present disclosure, which also fall within the scope of the disclosure.

The term "gas" as used in the present specification and claims refers to gases in which atoms or molecules are capable of capturing additional electrons to form electronegative ions. Other technical and scientific terms in this specification have the general meaning known in the art.

An example of the present disclosure which provides alternating current corona discharge field or positive corona discharge field by using an electrode is described below. It should be understood that the present disclosure is not limited thereto and if the electrode is capable of generating a plasma discharge in a sufficiently high energy state to generate electrons, it can also be used in the present disclosure.

FIG. 1 is a schematic view showing a specific configuration of an apparatus for plasma aided gas phase reaction according to the present disclosure. In the corona discharge dual-electric field, the reaction gas preferentially passes through a high frequency alternating current corona discharge field or a high frequency high voltage positive direct current corona discharge field, and is converted into positive ions and free radicals in the electric field, and then passes through a high frequency high voltage negative direct current corona discharge field, and is reduced and converted into a product in the electric field.

In one embodiment of the apparatus of the present disclosure, the reactor has a corona discharge dual-electric field, i.e., a high frequency alternating current corona discharge field or a high frequency high voltage positive direct current corona discharge field and a high frequency high voltage negative direct current corona discharge field. The voltage is a high voltage, for example, 15,000 volts. The high frequency is a high frequency voltage, for example, 25 kHz. In the reactor, there is an electrode or an anode in the region of the high frequency alternating current corona discharge field or the high frequency high voltage positive direct current corona discharge field, and an electrode or cathode in the region of the high frequency high voltage negative direct current corona discharge field. The two corona discharge fields can provide a sufficiently high energy, for example 5 eV, to convert the gas molecules. Apparatus 117 has an outer housing that can be made of carbon steel, stainless steel or other suitable materials.

Two cylinder or tubular reaction chambers 111 and 118 are disposed within the apparatus 117 formed by the outer housing, wherein the material of the cylindrical or tubular reaction chamber may be made of stainless steel, carbon steel or copper and other metals. The center of each cylindrical or tubular reaction chamber is provided with center electrodes 112 and 116, which are needle-like or saw tooth rod electrodes with tips. The center electrode 116 in the first electric field applies a high frequency positive direct current voltage (or alternating current) to generate a high frequency high voltage positive direct current corona discharge field (or high frequency alternating current corona discharge field). A high frequency negative direct current voltage is applied to the center electrode 112 in the second electric field to generate a high frequency high voltage negative direct current corona discharge field. The voltage (strength) is selected to satisfy the condition that the gas delivered to the apparatus can be highly ionized in the metal cylindrical or metal tubular reaction chambers 111 and 118.

An insulating medium tube 122 is disposed between the center electrode and the cylinder to form a dielectric barrier discharge (DBD) in the electric field, and provide a narrow collision reaction zone to enhance the decomposition of all molecules into free radicals or ions, thereby forming product molecules, enhancing the electric field strength of the plasma-aided reaction process. The material of the insulating medium tube 122 is, for example, glass, ceramic, silicone, polytetrafluoroethylene sheet or the like.

The electrode material of the center electrodes 112 and 116 may be nickel, iron, steel, tungsten, copper, silver, carbon or platinum, or any other material that can be used for the electrodes and generates corona around the electrodes to generate electrons. The electrode can also be coated with a metal catalyst. Available precious metal catalysts are: gold, nickel, ruthenium, cobalt, ruthenium and platinum. Any precious metal catalyst capable of generating electrons can be used.

During operation, when the center electrode 116 is energized by an alternating current corona discharge field or a positive corona discharge field source, a positive corona is generated at the tip end of the center electrode 116 to generate a positive corona field discharge, and high energy electrons hit the gas molecules. If an insulating medium tube 122 is added, a DBD can be formed to enhance the electric field strength to enhance the oxidation reaction. When the center electrode 112 is energized by the negative corona discharge field source, a negative corona is generated at the tip end of the center electrode 112 to generate a negative corona field discharge, mainly for the reduction and reforming reaction.

The high voltage electricity is supplied to the center electrodes 112 and 116 through the cable electrode distribution plates 115 and 123 for discharge. The two cylindrical or tubular reaction chambers 111 and 118 are connected to the counter electrodes 120 and 121, respectively. The outer housing of the apparatus 117 is connected to the ground.

Gas filters 127, 128 and 129 are provided at the opening 113 at the bottom of the apparatus, the opening 110 at the top of the apparatus, and the junction of the two electric fields, respectively, which can be used for a gas filter having the function of adsorbing harmful chemicals and particles.

The gas mixture is fed into the corona discharge dual-electric field in the apparatus through the opening 113 at the bottom of the apparatus. Some gas molecules can receive the discharged electrons for oxidation and reforming in a high frequency alternating current corona discharge field or a high frequency high voltage positive direct current corona discharge field. In the high frequency high voltage negative direct current corona discharge field, the gas oxide or ions can be reduced and converted again. The product is removed through the opening 110 at the top of the apparatus and is vapor-liquid separated by a condenser 133 where liquid can be discharged through port 125 and gas can be discharged through port 124.

In a preferred embodiment of the present application, the center electrode 116 is connected to the positive electrode of the positive corona discharge field source, and the counter electrode 120 opposite to the center electrode 116 is disposed on the outer wall of the reaction chamber and connected to the negative electrode of the positive corona discharge field source, generating a strong positive electric field within the positive corona discharge field. The center electrode 112 is connected to the negative electrode of the negative corona discharge field source, and the counter electrode 121 opposite to the center electrode 112 is disposed on the outer wall of the reaction chamber and connected to the positive electrode of the negative corona discharge field source, generating a strong negative electric field within the negative corona discharge field.

In a preferred embodiment of the present application, the center electrode 116 is connected to the positive electrode of the positive corona discharge field source, and the counter electrode 120 is grounded, generating a weak positive electric field within the positive corona discharge field. The center electrode 112 is connected to the negative electrode of the negative corona discharge field source, and the counter electrode 121 is grounded, generating a weak negative electric field within the negative corona discharge field.

With the above apparatus, the gas of different sources can be reformed, and according to the strength of the electric field, for example, organic compounds such as aliphatic hydrocarbons, higher carbon ethers, higher carbon alcohols, higher carbon esters, and the like, and inorganic compounds such as $N_2$, $O_2$, $H_2SO_4$, $NH_3$, and the like are produced in a strong electric field, for example, lower carbon alcohols are produced in a weak electric field.

In a preferred embodiment of the present application, the flue gas (which is composed of nitrogen, carbon oxides (such as carbon dioxide, carbon monoxide), oxygen, water vapor, nitrogen oxides (such as nitrogen monoxide, nitrogen dioxide) and sulfides (such as hydrogen sulfide, sulfur dioxide), inorganic pollutants, and the like, accounted for more than 99%, and the contents of dust, powder and sulfur dioxide being less than 1%) and water vapor are introduced into the above apparatus. In the apparatus, the center electrode 116 is connected to the positive electrode of the alternating current corona discharge field or the positive corona discharge field source, and the counter electrode 120 is grounded, generating a weak positive electric field in the alternating current corona discharge field or the positive corona discharge field. The center electrode 112 is connected to the negative electrode of the negative corona discharge field source, and the counter electrode 121 is grounded, generating a weak negative electric field in the negative corona discharge field.

Specifically, high energy electrons are provided by passing through an alternating current corona discharge field or a positive corona discharge field first, then a negative corona discharge field to carry out gas reactions. In the region of the alternating current corona discharge field or positive corona discharge field, high energy electrons or high energy positive charges are provided to decompose gas molecules, which can be activated to undergo decomposition and oxidation reactions to generate various components. Specifically, mainly in the alternating current electric discharge field or positive electric discharge field, electrons are collided with $H_2O$ steam to generate OH and H atoms or $H_2$, $CO_2$ reacts with electrons to generate CO and $O_2^-$, sulfide $SO_2$ with electrons reacts with $H_2O$ and oxygen $O_2$ to produce $H_2SO_4$ sulfuric acid liquid, nitrogen oxides $NO_x$ are decomposed with electrons, and may form N and O radicals; in the second subsequent negative corona discharge field, the electric cathode with high negative potential conducts corona discharge to release electrons, and CO and $H_2$ gas molecules capture these high energy electrons to form high energy electronegative gas ions, for example to form negative ions such as $H^-$, $CO^-$ or $H^-$ etc., and these negative ions will be reformed and reduced to form ethanol and methanol, so as to achieve the minimum system energy. Moreover, N and O radicals generate $N_2$ and $O_2^-$. The specific reactions are as follows: carbon oxides, nitrogen oxides and sulfides in the flue gas may undergo but are not limited thereto the following main reactions with the added water vapor, as well as the oxygen contained in the flue gas in the alternating current or positive corona discharge field:

$$CO + H_2O + e^- ====> CO_2 + H_2^-$$

$$2CO_2 + e^- ====> 2CO + O_2^-$$

$$2SO_2 + 2H_2O + 3O_2 + 2e^- 2e^- ====> 2H_2SO_4 + 2O_2^-$$

$$NO_x + e^- ====> +N.+xO.+e^-$$

$$2H_2S+3O_2+e^-====>2SO_2H_2O+e^-$$

In the subsequent negative corona discharge field, the main chemical reaction process is that carbon monoxide and charged hydrogen negative ion will spontaneously synthesize ethanol and methanol, and release negative oxygen ions:

$$H_2+2e^-====>2H^-<===>H_2^-$$

$$4CO+6H_2^-==>2C_2H_5(OH)+O_2^-+5e^-$$

$$CO+2H_2^-==>CH_3(OH)+2e^-$$

$$2N_2+2O_2+e^-====>N_2+O_2^-$$

According to the above principle, the apparatus of the present disclosure can purify and recycle industrial exhaust gas including the above flue gas, for example refinery waste gas, automobile or internal combustion engine exhaust gas, and coke oven gas, water gas and syngas do not need any other additional reaction gas because of the hydrogen source contained therein, the dual-electric field apparatus of the disclosure utilizes a hydrogen source to convert CO and $CO_2$ into organic or inorganic compound, to convert nitrogen oxides into an inert gas, and to convert sulfide into easily separated or easily removed sulfuric acid droplets, which can clean and purify the environment, as well as turn waste into treasure.

In a preferred embodiment of the present application, the water gas and/or syngas (which is composed of $CO_2$ of 5%, $H_2$ of 50%, CO of 40%, $N_2$ of 5%) specifically react(s) in the dual-electric field (the center electrode 116 is connected to the positive electrode of the alternating current corona discharge field or the positive corona discharge field source, and the counter electrode 120 is grounded, generating a weak positive electric field in the alternating current corona discharge field or the positive corona discharge field. The center electrode 112 is connected to the negative electrode of the negative corona discharge field source, and the counter electrode 121 is grounded, generating a weak negative electric field in the negative corona discharge field) of the present disclosure as follows: $CO_2$ therein will undergo the following main reaction in the alternating current or positive corona field:

$$2CO_2+e^-====>2CO+O_2^-$$

In the negative corona discharge field, carbon monoxide and charged hydrogen negative ion will spontaneously synthesize ethanol and methanol, and release negative oxygen ions:

$$H_2+2e^-====>2H^-<===>H_2^-$$

$$4CO+6H_2^-====>2C_2H_5OH+O_2^-+5e^-$$

$$CO+2H_2^-====>CH_3(OH)+2e^-$$

In a preferred embodiment of the present application, the apparatus of the present disclosure not only can reform an exhaust gas such as flue gas, but also can reform a main source of carbonaceous energy containing $CH_4$, such as coal-bed gas. Methane in the coal-bed gas may undergo but not limited thereto the following main reactions with the added water vapor, as well as the oxygen contained in the coal-bed gas in the alternating current or positive corona discharge field:

$$CH_4+H_2O+3e^-====>CO+3H_2^-$$

$$CH_4+\tfrac{1}{2}O_2+2e^-====>CO+2H_2^-$$

$$CO+H_2O+e^-====>CO_2+H_2^-$$

$$2CO_2+e^-====>2CO+O_2^-$$

In the subsequent negative corona discharge field, the main chemical reaction process is the same as those of the above flue gas, i.e., carbon monoxide and charged hydrogen negative ion will spontaneously synthesize ethanol and methanol, and release negative oxygen ions.

$$H_2+2e^-====>2H^-<===>H_2^-$$

$$4CO+6H_2^-==>2C_2H_5(OH)+O_2^-+5e^-$$

$$CO+2H_2^-==>CH_3(OH)+2e^-$$

According to the above principle, the apparatus of the present disclosure can reform and purify any gas source containing a carbon source. The main component $CH_4$ in the gases, such as coalbed gas, refining gas, shale gas, biogas, etc. is reformed, biogas does not require the addition of other gas reactants, since as the main components, methane and $CO_2$ can be reformed in the dual-electric field.

In a preferred embodiment of the present application, the shale gas mainly reacts with $O_2$ or $CO_2$ in the alternating current or positive corona field as follows:

$$CH_4+\tfrac{1}{2}O_2+2e^-====>CO+2H_2^-$$

$$CH_4+CO_2+2e^-====>2CO+2H_2^-$$

In the negative corona discharge field, the main chemical reaction process is that carbon monoxide and charged hydrogen negative ion will spontaneously synthesize ethanol and methanol, and release negative oxygen ions:

$$H_2+2e^-====>2H^-<===>H_2^-$$

$$4CO+6H_2^-==>2C_2H_5(OH)+O_2^-+5e^-$$

$$CO+2H_2^-==>CH_3(OH)+2e^-$$

In a preferred embodiment of the present application, methane and $CO_2$, as the main components of the biogas, mainly react in the alternating current or positive corona discharge field as follows:

$$CH_4+CO_2+2e^-====>2CO+2H_2^-$$

In the negative corona discharge field, the main chemical reaction process is that carbon monoxide and charged hydrogen negative ion will spontaneously synthesize ethanol and methanol, and release negative oxygen ions:

$$H_2+2e^-====>2H^-<===>H_2^-$$

$$4CO+6H_2^-==>2C_2H_5(OH)+O_2^-+5e^-$$

$$CO+2H_2^-==>CH_3(OH)+2e^-$$

Accordingly, when the dual-electric field in the plasma gas conversion apparatus provided by the present disclosure is a weak electric field, it can be used to prepare ethanol and/or methanol. Specifically, the apparatus converts a carbon source-containing gas, for example, $CH_4$ and/or CO, $CO_2$, and the like, into ethanol and methanol. The positive-negative corona dual-electric field or the alternating current-negative corona dual-electric field apparatuses of the present disclosure can be arranged in series, and the unreacted $CH_4$ or CO, $CO_2$ in the product mixture can be passed to the next dual-electric field apparatus, optionally with the addition of additional water vapor or hydrogen to further convert the reaction gas to the final product. Such a cyclic conversion can achieve a very high gas conversion rate. For example, methane is reformed with the above-described dual-electric field apparatus of the present disclosure. In the alternating current corona discharge field or positive corona discharge field, the conversion ratio of methane to syngas i.e., CO and $H_2$ can reach 45%, and in the subsequent second electric field of the negative corona discharge field, syngas can be converted to ethanol in a conversion ratio of up to 90% or more. If four reactors are used in series, the conversion of methane can reach 95% or more.

When the dual-electric field in the plasma gas conversion apparatus provided by the present disclosure is a strong electric field, it can be used for preparing organic compounds such as aliphatic hydrocarbons, higher carbon ethers, higher carbon alcohols, higher carbon esters, and inorganic compounds such as $N_2$, $O_2$, $H_2SO_4$, $NH_3$, and the like.

In a preferred embodiment of the present application, CO and water vapor are introduced into the aforesaid apparatus, wherein in the reaction chamber 118, the center electrode 116 is connected to the positive electrode of the positive corona discharge field source, and the counter electrode 120 is connected to the negative electrode of the positive corona discharge field source, generating a strong positive electric field in the positive corona discharge field. In the reaction chamber 111, the center electrode 112 is connected to the negative electrode of the negative corona discharge field source, and the counter electrode 121 is connected to the positive electrode of the negative corona discharge field source, generating a strong negative electric field in the negative corona discharge field. At this time, the main components into which CO and water vapor are reformed in the reactor are $C_7$-$C_{20}$ organic compounds, and the main components include heptane, diethyl phthalate, diisooctyl phthalate and the like.

In a preferred embodiment of the present application, the aforesaid center electrode 112 is a stainless steel electrode, and the counter electrode 121 of the outer wall of the reaction chamber 111 is connected to the positive electrode of the power supply. Inside the steel pipe between the positive electrode and the negative electrode, a silicone tube abutting against the inner wall of the reaction chamber 111 and a thin glass tube covering the stainless steel negative electrode (center electrode 112) are inserted as an insulating medium tube. Between the two medium tubes, titanium dioxide particles are filled as a third layer of insulating medium to form a dielectric barrier structure of the slit sandwich. In such a reactor, reactions are carried out to produce $C_3$-$C_{20}$ organic compounds, and the main components include propane, methyl benzyl alcohol, hexadecane, octadecane, and the like.

The embodiments of the present disclosure have been described above. However, the present disclosure is not limited to the above-described embodiments. Any modifications, equivalent substitutions, improvements, and the like within the spirit and principles of the disclosure are intended to be included within the scope of the present disclosure.

The invention claimed is:

1. A method for the plasma dual-electric field aided gas phase reactions, comprising:
    generating a first electric field that is an alternating current corona discharge field or a positive corona discharge field;
    generating a second electric field that is a negative corona discharge field;
    passing a reaction gas stream successively through the first electric field and the second electric field to form a product gas stream,
    wherein the first electric field and the second electric field are disposed in a reactor, and
    wherein the reaction gas stream comprises one or more compounds chosen from $CH_4$, CO, $H_2$, $H_2S$, or NO, and one or more compounds chosen from $CO_2$, $O_2$, $H_2O$, $SO_2$, or $NO_2$, and the product gas stream comprises one or more compounds chosen from aliphatic hydrocarbons, ethers, alcohols, $H_2SO_4$, or $N_2$.

2. The method according to claim 1, wherein the positive corona discharge field is a high voltage positive direct current corona discharge field, and the negative corona discharge field is a high voltage negative direct current corona discharge field.

3. The method according to claim 1, further comprising adjusting an intensity of the first electric field, an intensity of the second electric field, or both to cause a change in a composition of the product gas stream.

4. The method according to claim 3, wherein adjusting the intensity of the first electric field is by adjusting a voltage of the first electric field, and adjust the intensity of the second electric field is by adjusting a voltage of the second electric field.

5. A dual-electric field apparatus, comprising:
    a housing having an inlet and an outlet,
    at least a first reaction chamber and a second reaction chamber disposed in the housing, wherein during operation, a reaction gas stream successively passes through the first reaction chamber and the second reaction chamber to form a product gas stream,
    wherein the first reaction chamber comprises a first electrode disposed inside the first reaction chamber and away from a wall of the first reaction chamber, a first insulating medium layer disposed between the first electrode and the wall of the first reaction chamber, wherein the first electrode is connected to an alternating current or a positive voltage source and the wall of the first reaction chamber is grounded,
    wherein the second reaction chamber comprises a second electrode disposed inside the second reaction chamber and away from a wall of the second reaction chamber, a second insulating medium layer disposed between the first electrode and the wall of the second reaction chamber,
    wherein the second electrode is connected to a negative voltage source and the wall of the second reaction chamber is grounded.

6. The apparatus according to claim 5, wherein, when energized, the first reaction chamber contains a first electric field between the first electrode and the wall of the first reaction chamber, and the second reaction chamber contains a second electric field.

7. The apparatus according to claim 5, wherein the first electric field is an alternating current corona discharge field or a positive corona discharge field, and the second electric filed is a negative corona discharge field.

8. The apparatus according to claim 7, wherein the first reaction chamber or the second reaction chamber has a tubular wall, and wherein the first electrode or the second electrode is a metal rod.

9. The apparatus according to claim 8, wherein the first insulating medium layer or the second insulating medium layer has a tubular shape, and is made of a material chosen from glass, ceramic, silica gel, wood, or bamboo.

10. The apparatus according to claim 8, comprising more than two reaction chambers.

11. The apparatus according to claim 5, further comprising a sensor installed in an intake line connected to the inlet for measuring a concentration of methane gas and oxygen in a fluid flowing into the inlet.

12. The apparatus according to claim 5, further comprising a condensing separator connected to the outlet for separating a fluid from the outlet into a gas stream and a liquid stream.

13. A method for preparing organic compounds, comprising:
   energizing the dual electric field apparatus of claim 5 to generate the first electric field in the first reaction chamber and to generate the second electric filed in the second reaction chamber;
   feeding a reaction gas stream into the inlet of the dual electric field apparatus; and
   obtaining a product gas stream from the outlet of the dual electric field apparatus,
   wherein the reaction gas stream comprises one or more compounds chosen from chosen from $CH_4$, $CO_2$, CO, $O_2$, $H_2O$ or $H_2$, and the product gas stream comprises one or more compounds chosen from aliphatic hydrocarbons, ethers, or alcohols.

14. A method for purifying a gas stream, comprising:
   energizing the dual electric field apparatus of claim 5 to generate the first electric field in the first reaction chamber and to generate the second electric filed in the second reaction chamber;
   feeding the gas stream into the inlet of the dual electric field apparatus; and
   obtaining a purified gas stream from the outlet of the dual electric field apparatus,
   wherein the reaction gas stream comprises one or more compounds chosen from $SO_2$, $H_2S$, NO, $NO_2$, or CO, and the product gas stream comprises one or more compounds chosen from $H_2SO_4$, $N_2$, or $CO_2$.

* * * * *